United States Patent
Kiefer et al.

(12) 
(10) Patent No.: US 6,180,839 B1
(45) Date of Patent: Jan. 30, 2001

(54) CONTINUOUS PREPARATION OF DIMETHYLVINYLCARBINOL BY ISOMERIZING PRENOL

(75) Inventors: Matthias Kiefer, Nussloch; Wolfgang Siegel, Limburgerhof; Jörg Therre, Worms; Melanie Pahl; Werner Aquila, both of Mannheim; Ulrich Schäfer-Lüderssen, Ludwigshafen, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/265,923

(22) Filed: Mar. 10, 1999

(30) Foreign Application Priority Data

Mar. 12, 1998 (DE) ............................................. 198 10 669

(51) Int. Cl.⁷ .................................................. C07C 27/00
(52) U.S. Cl. ............................................................. 568/906
(58) Field of Search ..................................... 568/906, 875

(56) References Cited

U.S. PATENT DOCUMENTS

| | | | |
|---|---|---|---|
| 2,373,956 | * 4/1945 | Hearne | 568/906 |
| 2,435,078 | * 1/1948 | Hearne | 568/906 |
| 3,355,505 | * 11/1967 | Tedeschi | 568/906 |
| 3,696,155 | * 10/1972 | Mueller | 568/906 |
| 5,998,680 | * 12/1999 | Kiefer | 568/906 |

FOREIGN PATENT DOCUMENTS

| | | |
|---|---|---|
| 1 925 197 | 11/1970 | (DE) . |
| 2 056 343 | 5/1972 | (DE) . |
| 0 860 415 | 8/1998 | (EP) . |
| 411471 | 7/1934 | (GB) . |

* cited by examiner

Primary Examiner—Michael L. Shippen
(74) Attorney, Agent, or Firm—Oblon, Spivak, McClelland, Maier & Neustadt, P.C.

(57) ABSTRACT

A process is described for the continuous preparation of dimethylvinylcarbinol (DMVC) by continuously reacting prenol with the aqueous solution of a protic acid in the still or in the lower part of a rectification column while distilling off the DMVC formed in the form of an azeotropic mixture with water, which comprises a) during the reaction ensuring that as far as possible no liquid two-phase mixture forms in the reaction mixture,
b) distilling off the DMVC which forms at a reflux ratio of at least 2, as a result of which there is virtually no more prenol present in the distillate from the column, and
c) setting the reaction volume and/or the amount of prenol added per hour and/or the concentration of protons in the reaction mixture in such a manner that the quotient, defined as residence time concentration coefficient, of the reaction volume and the volume of prenol added per hour multiplied by the concentration of protons in the reaction mixture has a value between 0.001 h·mol/l and 1 h·mol/l.

Figure 1:
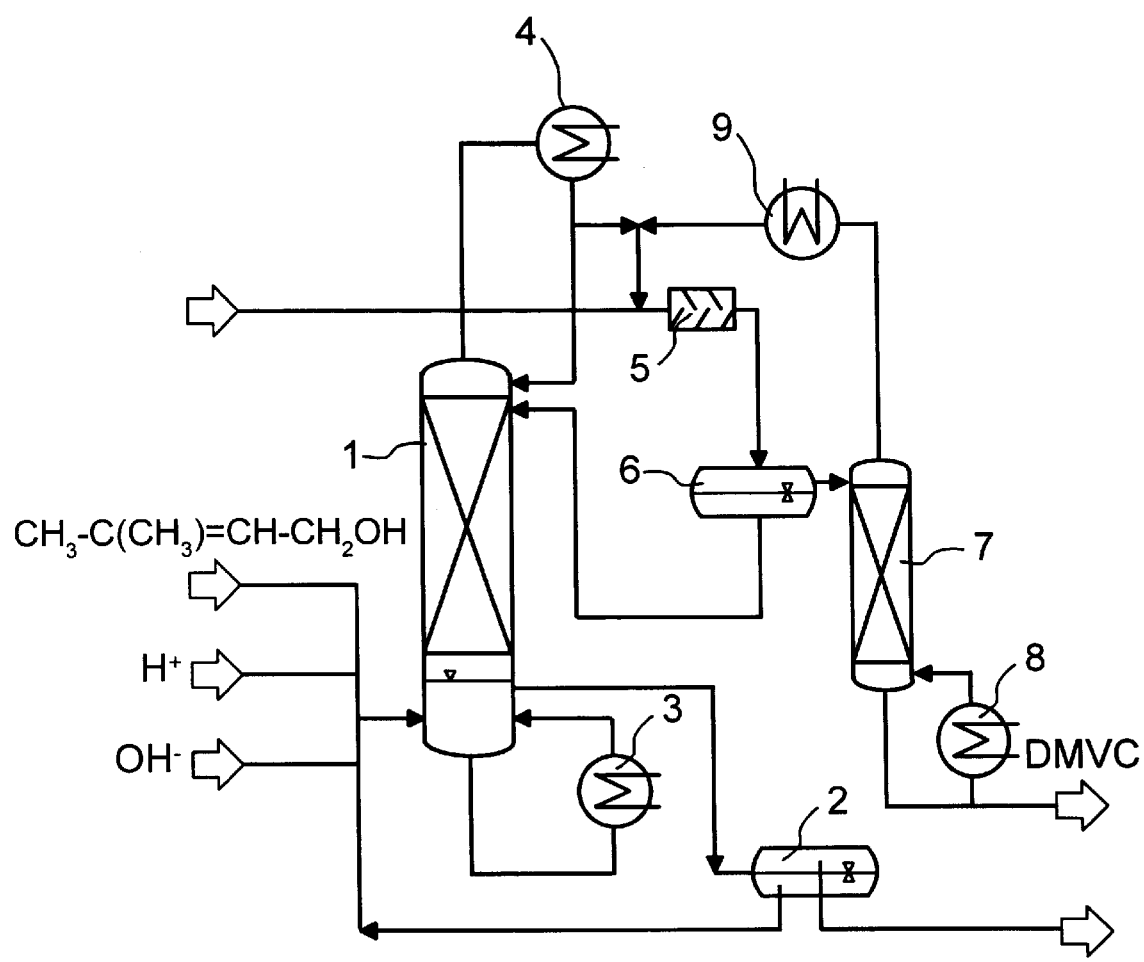

In this connection, the formation of a liquid two-phase mixture in the reaction mixture is prevented, in addition to avoiding too large a prenol excess, by continuously taking from the reaction mixture a partial stream, passing it over a phase separation vessel, completely or at least largely removing there the small quantities, formed in the course of the reaction, of organic by-products which are insoluble or only partially soluble in water, and returning the aqueous phase to the reaction volume.

11 Claims, 3 Drawing Sheets

CONTINUOUS PREPARATION OF DIMETHYLVINYLCARBINOL BY ISOMERIZING PRENOL

The present invention relates to a continuous process for the preparation of dimethylvinylcarbinol by isomerizing prenol in aqueous solution in the presence of protic acids.

Dimethylvinylcarbinol (DMVC; 2-methyl-3-buten-2-ol) is an important intermediate in industrial organic chemistry and serves in particular as an intermediate for the preparation of fragrances or else as an additive in soaps and detergents.

It is known that 3-methyl-2-buten-1-ol (prenol) can isomerize under acid catalysis to DMVC. This isomerization corresponds to a 1,3 migration of the hydroxyl group and a corresponding shift of the double bond, as is shown in the equation below:

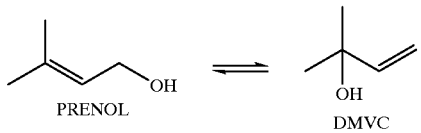

PRENOL ⇌ DMVC

This migration of a double bond and of a substituent is known for allyl compounds and is generally referred to as allyl rearrangement. Allyl rearrangements of allyl alcohols are equilibrium reactions.

A general overview of the isomerization of allyl alcohols, catalyzed by protic acids, can be found, for example, in Houben-Weyl: "Methoden der organischen Chemie" [Methods in Organic Chemistry], volume VI, 1b, page 528 et seq., Stuttgart, 1984. This describes, inter alia, that such isomerizations can be carried out in a particularly simple manner, the corresponding primary alcohol having an internal C=C double bond being formed from a tertiary allyl alcohol having a terminal C=C double bond.

In keeping with this knowledge, in the past, the isomerization of DMVC, a tertiary allyl alcohol, has in particular been used industrially to give its isomer, prenol, a primary allyl alcohol. Both compounds have, for example, been used in the fragrance industry as base substance for the preparation of alcohols of the terpene series. Based on the earlier widespread industrial carbide-acetylene chemistry, dialkylalkenylcarbinols, such as DMVC, were readily accessible by base-induced condensation of 1-alkynes, such as acetylene, with ketones, such as acetone, and subsequent hydrogenation of the triple bond to a double bond. Nowadays, acetylene is a comparatively rare and expensive raw material. On the basis of petrochemical raw materials which is common nowadays, olefins such as dialkylalkenes, such as isobutene, are by contrast readily accessible. These can be processed by condensation with aldehydes, such as formaldehyde, and subsequent isomerization of the double bond readily to give prenol or prenol derivatives, such as prenol substituted by organic radicals. In industry, there is thus nowadays a particular need for a process which can be used to prepare the tertiary allyl alcohol DMVC from the primary allyl alcohol prenol.

SU-A 181 090 describes a process for the preparation of DMVC by dehydration of 3-methyl-1,3-butanediol, in which a mineral acid, in particular sulfuric acid, in a concentration below 1% by weight (corresponding to a pH above 0.7), preferably in a concentration of from 0.3 to 0.5% by weight, is used as catalyst. This preferred concentration range corresponds to a pH range from 1.0 to 1.2. This publication also teaches that it is also possible to use the isomeric alcohols $C_5H_9OH$ (3-methyl-3-buten-1-ol and prenol) as starting materials in this process. Furthermore, the example given shows that when the disclosed process is carried out, high amounts of by-products are produced, which must be regularly removed discontinuously from the reactor. The yield of DMVC from 3-methyl-1,3-butanediol is only 70%. Yield data for the process variant mentioned starting from prenol are not given. Similarly, there is no information regarding the relationship between acid concentration, reaction volume and input flow rate of fresh prenol.

According to J. Gen. Chem. USSR, 21 (1951) pages 1235–1241, A. I. Lebedeva and L. L. Schukovskaya investigated the dependency of the isomerization of DMVC on the pH of the reaction medium and on the reaction temperature used for a reaction time of 30 hours. They found that isomerization of the DMVC used took place at room temperature only at a pH of 1.29 or below. At a pH of 1.32 or above, no isomerization of the DMVC was observed either at room temperature or in a boiling water bath. The discontinuous process has a complicated workup which cannot be utilized economically on an industrial scale.

In Bull. Acad. Sci. USSR, Chem. Ser. 1946, 419–426, I. N. Nazarov, I. N. Azerbaev and V. N. Rakcheeva teach that the isomerization of dialkylvinylcarbinols, i.e. the tertiary allyl alcohols, into the corresponding primary allyl alcohols proceeds "quite smoothly" in a temperature range from 60 to 100° C. under the influence of 0.1% strength by weight sulfuric acid, i.e. at a pH of about 1.7, while at room temperature the isomerization is carried out under the influence of 1–5% strength sulfuric acid, i.e. at a pH of about 0.7 and below. This publication also teaches that in the case of a sulfuric acid concentration of 0.01%, i.e. a pH of 2.7, the isomerization process itself proceeds too slowly at a temperature of 100° C. Thus, all of the known examples for the isomerization of allyl alcohols were carried out with high acid concentrations, i.e. a low pH of no more than 1.5 or even significantly below 1. The described process is unsuitable for the economic preparation of DMVC.

JP-A-54/061110 describes a process for the isomerization of allyl alcohols using large amounts of boric acid as catalyst. From 0.1 to 60% by weight, in particular from 1 to 30% by weight, of boric acid are used. Conversions above 90% are only achieved with boric acid concentrations above 7% by weight of boric acid; at even higher amounts of boric acid the selectivity of the isomerization drops rapidly. The achieved yields are below 85%. No information is given regarding the type of column used and the reflux ratio used. The examples show that the DMVC obtained was contaminated with prenol. The described workup is very complicated. It is not possible to use the described process to prepare DMVC from prenol economically.

A disadvantage of all of the known processes for the isomerization of allyl alcohols was that they produce relatively large amounts of undesired by-products.

There continued to be, therefore, a great need for a process which enables a continuous preparation of pure DMVC from prenol in a simple, inexpensive and very selective manner but with high space-time yields.

Accordingly, the invention provides a process for the continuous preparation of dimethylvinylcarbinol (DMVC) by continuously reacting prenol with the aqueous solution of a protic acid in the still or in the lower part of a rectification column while distilling off the DMVC formed in the form of an azeotropic mixture with water, which comprises a) during the reaction ensuring that as far as possible no liquid two-phase mixture forms in the reaction mixture, b) distilling off the DMVC which forms at a reflux ratio of at least 2 and c) setting the reaction volume and/or the amount of prenol added per hour and/or the concentration of protons in the reaction mixture in such a manner that the quotient, defined as residence time concentration coefficient, of the reaction volume and the volume of prenol added per hour multiplied by the concentration of protons in the reaction mixture has a value between 0.001 h·mol/l and 1 h·mol/l, preferably from 0.01 to 0.15 h·mol/l.

Only when it is ensured that as far as possible no liquid two-phase mixture forms in the reaction mixture is the formation of by-products largely suppressed.

In order to prevent the formation of a liquid two-phase mixture in the reaction mixture, in addition to using quantities of prenol which are not too large, it is important to continuously take from the reaction mixture in the reaction volume a partial stream, pass the latter over a phase separation vessel, completely or at least largely remove there the small quantities of organic substances formed which are insoluble or only partially soluble in water, and then return the aqueous phase to the reaction volume.

An important factor for the desired high DMVC yield is the presence of a sufficiently high heating capacity to distil off the DMVC which forms at a reflux ratio of at least 2, as a result of which there is usually virtually no more prenol present in the distillate from the column.

It is advantageous to distil off the DMVC at a reflux ratio of from 2 to 25, preferably from 4 to 20.

The distillate obtained at the head of the column can be worked up by simply bringing it into close contact with an extractant which is only partially miscible with water and separating the organic phase which forms from the aqueous phase. The aqueous phase which has been separated off is advantageously returned immediately to the reaction volume and particularly preferably deposited as reflux at the head of the isomerization column.

The resulting organic phase can be separated in a simple manner in a rectification column, a mixture of a little DMVC, water and the extractant being obtained at the head thereof and pure DMVC being obtained from the still thereof.

The isomerization is particularly advantageously carried out in a column having from 6 to 40 theoretical plates.

Suitable internals for the isomerization column and the rectification column include packing, differently arranged column plates or else structured packings made of-sheet metal or metal cloth.

The novel process can be carried out particularly advantageously if the pH of the aqueous solution of protic acid is adjusted to between 1.2 and 3.5 depending on the reaction volume and the volume of prenol added per hour.

The process is shown diagrammatically in FIG. 1 and is described below.

The prenol to be reacted is added to column 1, the isomerization column, which contains from 3 to 55, preferably from 5 to 50, in particular from 6 to 40, theoretical plates. It is preferably added to the still of the column, but can also be added to the lower part of this isomerization column. In some circumstances, it may also be favorable to add the prenol to containers or apparatuses attached to the still of the column. If desired, the still of the column can be increased by one container in order to provide a larger reaction volume.

The still of the column 1 is filled with a solution consisting largely of water, which contains an accurately measured concentration of protons ($H^+$ ions). The concentration of protons can be determined easily by measuring the pH of the solution or by titration. In some circumstances, the installation of an online pH meter is advantageous. In accordance with this invention, the concentration of protons should be set such that the residence time concentration coefficient is between 0.001 h·mol/l and 1 h·mol/l and is in particular between 0.005 h·mol/l and 0.25 h·mol/l, the residence time concentration coefficient (abbreviated to RTCC) being defined as the quotient of the reaction volume and the volume of prenol added per hour, multiplied by the concentration of protons: residence time concentration coefficient= (reaction volume/input of prenol per hour) times the concentration of protons in mol per liter.

For the purposes of the invention, reaction volume is taken to mean the volume of the isomerization column filled with liquid where prenol, water and acid make contact and thus the rearrangement to DMVC proceeds. If the acid which is added to the still of the column is nonvolatile under reaction conditions, the reaction volume is usually the volume of the still of the isomerization column with connected evaporators, containers and pipework. This volume can be determined easily by measuring the apparatus and pipework.

If a nonvolatile acid is added above the still of the column or a volatile acid is used, the isomerization column can also be operated as a reaction column, in which case the liquid in the column body then additionally serves as reaction volume and must be included in the calculation.

The volumetric input of fresh prenol into the equipment can be determined simply and accurately using customary measuring instruments.

If the concentration of protons is too low, it can be increased in a simple manner by adding acids or acid mixtures or buffers.

In the novel process, it is possible to use virtually any proton acids which can produce the required proton concentration in the reaction mixture in order to keep the residence time concentration coefficient in the claimed range, which is a prerequisite for the process to be carried out in an advantageous manner. For example, the acids listed below or mixtures of these acids may be mentioned: hydrofluoric acid, hydrochloric acid, perchloric acid, hydrobromic acid, sulfuric acid, sulfonic acids, salts of the hydrogensulfate ion, such as potassium hydrogensulfate or sodium hydrogensulfate, nitric acid, phosphoric acid and salts of the dihydrogenphosphate, such as potassium dihydrogenphosphate and sodium dihydrogenphosphate. Other examples of acids which can be used are the stronger organic acids, such as formic acid, oxalic acid, tartaric acid, succinic acid, maleic acid, fumaric acid, adipic acid and citric acid. Equally so, it is possible to use salts of polybasic acids in which acid functions are also present. Examples thereof are alkali metal salts of polybasic carboxylic acids, such as monosodium oxalate, monosodium tartrate, monosodium succinate, monosodium adipate, monosodium citrate, disodium citrate or the corresponding potassium compounds. It is just as possible to use a polymeric and polyfunctional acid. Such acids are known under the name acid ion exchangers and are commercial products which are widely available. When solid ion exchangers are used, it is advantageous to arrange these as a fixed bed in a loop reactor attached to the column 1.

The protic acids used are particularly advantageously hydrochloric acid, sulfuric acid, nitric acid and phosphoric acid, in particular phosphoric acid, since this is low in cost and noncorrosive.

If the concentration of protons is too high, it can be lowered by adding bases.

Examples of bases which can be employed, which can be used where appropriate as aqueous solutions, are: sodium hydroxide, potassium hydroxide, calcium hydroxide or amines, such as alkylamines or else mixtures of these bases.

In addition, in the novel process, it is also possible to adjust the concentration of protons using an acid in a mixture with its conjugated base, i.e. a buffer. Suitable buffer mixtures which can be readily adjusted to be in the novel pH range for the reaction are, for example: phosphoric acid/sodium phosphate, lactic acid/sodium lactate, citric acid/sodium citrate, disodium citrate/HCl, potassium hydrogenphthalate/HCl and disodium hydrogenphosphate/citric acid.

Over the course of the operation of the isomerization column 1, by-products form which are insoluble or virtually insoluble in water, but in amounts which are small due to the high selectivity of the process. These by-products must be removed if the yields and purities of the DMVC are to be optimized. They are preferably removed from the process by drawing off a portion from the reaction mixture and adding it to the phase separation vessel 2. There, the by-products separate out as the upper phase, are removed and disposed of, for example, by combustion. The aqueous phase which has largely been freed from the by-products can be returned to the isomerization column 1.

The still of the isomerization column is heated with steam via the evaporator 3, and the vapors (exhaust steam) leaving the head of the isomerization column are condensed in the condenser 4. The DMVC which forms is advantageously distilled off at a reflux ratio of from 2 to 25, preferably from 4 to 20. The reflux ratio should be chosen such that the distillate obtained at the head of the column does not contain prenol. This can be established readily by gas chromatographic analysis or by observing the temperature profile of the isomerization column 1.

The vapors (exhaust steam) obtained at the head of the isomerization column, or the distillate obtained therefrom by condensation, generally consists of approximately 74% by weight of DMVC, approximately 25% by weight of water and approximately 1% by weight of isoprene and does not contain prenol. For work-up, the distillate is combined with a stream which consists of a little water, DMVC, isoprene and an extractant.

Suitable extractants are organic solvents which are immiscible or only partially miscible with water and which have a boiling point at atmospheric pressure above 30° C. and below 200° C., preferably below 120° C. and in particular below 100° C. Examples of such extractants which may be mentioned are open-chain, branched or cyclic dialkyl ethers, such as diethyl ether, dibutyl ether, tert-butyl methyl ether or tert-butyl ethyl ether, aliphatic, alicyclic or aromatic hydrocarbons, such as isoprene, pentane, hexane, cyclopentane, cyclohexane, benzene, toluene or the xylols or mixtures of extractants, such as light gasolines or kerosine. The two streams are intensively mixed in the static mixer 5 or else using a stirrer, and the mixture is introduced into the phase separation vessel 6. The aqueous phase which separates out is returned to the isomerization column 1. The organic phase which separates out is introduced into the rectification column 7, also called the purification column, fitted with the evaporator 8 and the condenser 9, and separated into one stream which consists of water, DMVC and the extractant and one stream which consists of pure DMVC. The stream containing the extractant is recombined with the distillate obtained from the isomerization column. The concentration of the extractant in the organic phase which separates out in the phase separator 6 is between 1% by weight and 99% by weight, in particular between 20% by weight and 80% by weight.

Figure 2:
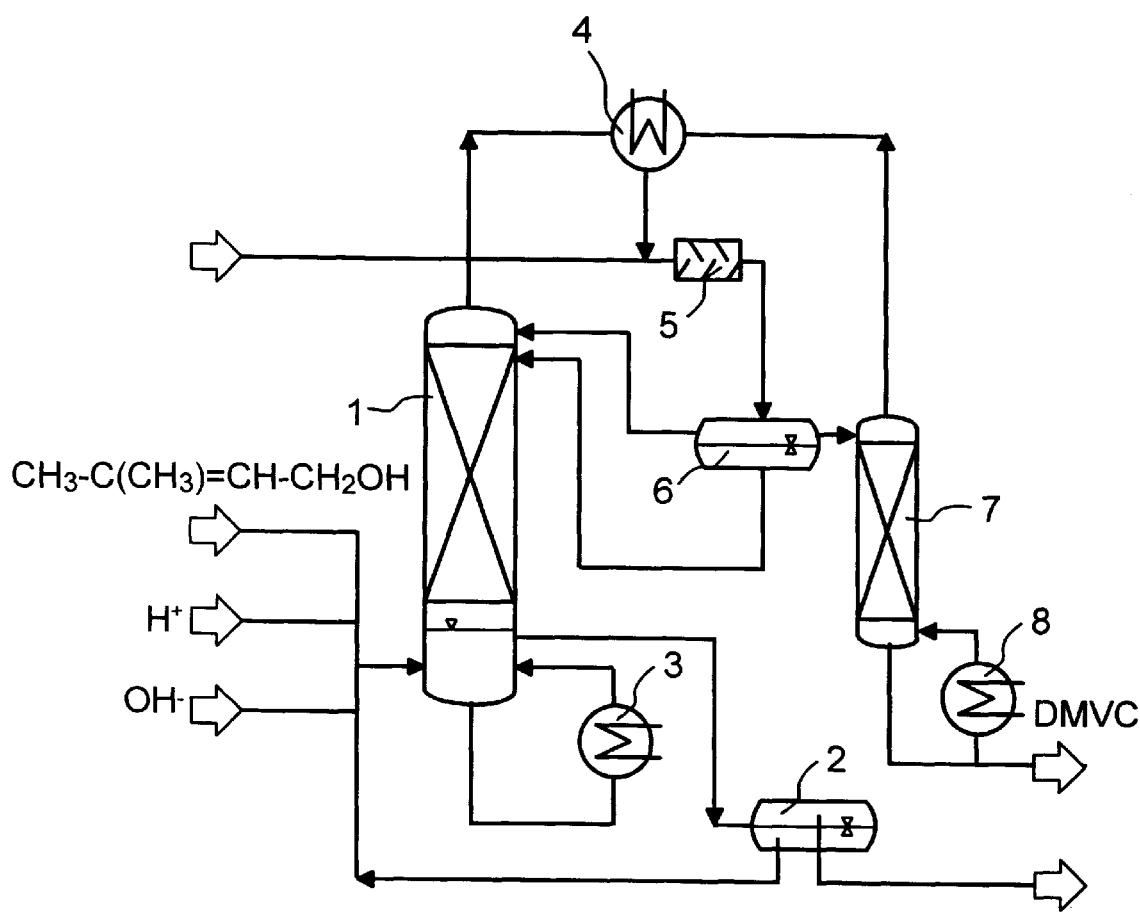

A variant of the novel process is shown diagrammatically in FIG. 2. In this process variant, the exhaust steam from the isomerization column and the exhaust steam from the purification column are condensed in a common condenser 4. As a result, it is possible to dispense with the condenser 9 shown in FIG. 1. In order to adjust the novel reflux ratio in the isomerization column, a stream is withdrawn from the organic phase of the phase separation vessel 6 and introduced at the head of the isomerization column.

The pressure in the isomerization column is generally between 0.1 bar and 10 bar, preferably between 0.8 and 1.5 bar.

The temperature in the still of the isomerization column is advantageously between 45° C. and 180° C., preferably between 90° and 110° C.

Figure 3:
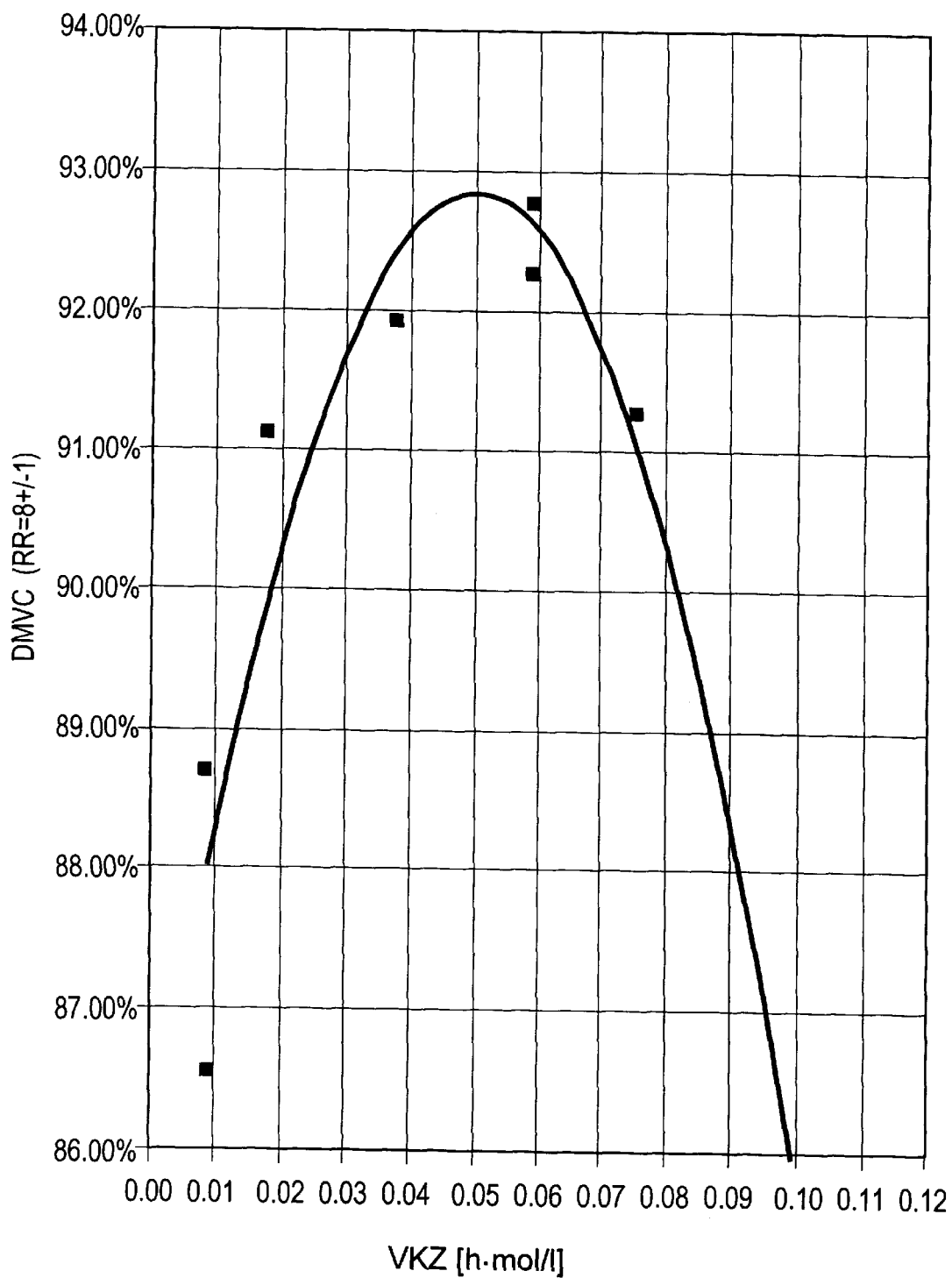

The novel process can be used to continuously prepare DMVC from prenol in a very high selectivity of up to 93.96%. This fact is all the more surprising as the conversion of prenol is 100%. The purity of the DMVC produced is extraordinarily high and is as a rule greater than 99%, even though the work-up of the DMVC is very easy to carry out even industrially. The process requires only a minimal amount of customary apparatus, which can be constructed from low cost and readily available materials, such as stainless steel, since corrosion is not usually a problem. The process produces only small amounts of waste which can be disposed of easily. Catalysts which may be used are small amounts of low cost and readily available acids, such as, in particular, phosphoric acid. A further very important advantage is that the process, for a uniform selectivity, can be adapted to fluctuating amounts of product by keeping the residence time concentration coefficient in the stated range by changing the proton concentration, and/or by changing the prenol added per hour and/or by changing the reaction volume. Surprisingly, it has been found that the yield exceeds a maximum with increasing residence time concentration coefficient. FIG. 3 shows, for example, the effect of the residence time concentration coefficient (RTCC) on the yield of DMVC at a reflux ratio (RR) of 8+/−1. By regulating the pH, it is possible to maintain this maximum even when the inputs of prenol are changing.

EXAMPLES 1 TO 27

Continuous Laboratory Experiments Using the Variant According to FIG. 1

The reaction volume of the isomerization apparatus 1 was filled at the start of the experiment with 660 ml of water and adjusted to the pH given in Table 1 or the stated hydrogen ion concentration ($H^+$ conc.) by adding phosphoric acid. The still of the column was heated to boiling and then the input of prenol was started. The amount of prenol introduced and the amount of DMVC produced were continuously determined by weighing. Cyclohexane was added as extractant at the head of the column in the phase separation vessel 6. The concentration of cyclohexane in the phase separator 6 at the head of the isomerization column 1 was 30% by weight. The yield of DMVC was determined as a quotient of the mass of the DMVC which had flowed off and the prenol which had been introduced. The purity of the DMVC obtained was determined by gas chromatography. The conversion of prenol was 100%. The experiment time was between 48 h and 96 h.

The process-essential values of Examples 1–27 are given in Table 1.

EXAMPLES 28 TO 30

Continuous Laboratory Experiments Using the Variant According to FIG. 2

The procedure was as described for Examples 1–27, except that the still of the isomerization column 1 used was a 4 l stirred vessel which was in each case filled with 3000 ml of reaction volume, and that, corresponding to the diagrammatic representation in FIG. 2, a common condenser for the two columns was used.

The process-essential data are likewise given in Table 1.

TABLE 1

| Example | pH | H+ concentration [mol/l] | Prenol input [ml/h] | Reaction volume [ml] | Residence time [h] | RTC coefficient [h · mol/l] | Reflux ratio | Circulated stream, still decanter [l/h] | DMVC yield | DMVC purity |
|---|---|---|---|---|---|---|---|---|---|---|
| 1 | 2.5 | 0.00316 | 117.6 | 660 | 5.61 | 0.0177 | 14.5 | 2.6 | 92.3% | 99.2% |
| 2 | 2.5 | 0.00316 | 117.6 | 660 | 5.61 | 0.0177 | 14.8 | 2.6 | 93.4% | 99.3% |
| 3 | 2.5 | 0.00316 | 117.6 | 660 | 5.61 | 0.0177 | 9.2 | 2.6 | 90.0% | 99.5% |
| 4 | 2.5 | 0.00316 | 117.6 | 660 | 5.61 | 0.0177 | 18.7 | 2.6 | 93.4% | 99.1% |
| 5 | 2.5 | 0.00316 | 117.6 | 660 | 5.61 | 0.0177 | 12.2 | 2.6 | 92.4% | 99.2% |
| 6 | 2.5 | 0.00316 | 117.6 | 660 | 5.61 | 0.0177 | 6.1 | 2.6 | 89.5% | 99.4% |
| 7 | 2.5 | 0.00316 | 117.6 | 660 | 5.61 | 0.0177 | 15.1 | 2.6 | 93.9% | 99.3% |
| 8 | 2.5 | 0.00316 | 235.3 | 660 | 2.81 | 0.0089 | 8.8 | 2.6 | 88.7% | 99.7% |
| 9 | 2.5 | 0.00316 | 235.3 | 660 | 2.81 | 0.0089 | 8.8 | 2.6 | 86.6% | 99.0% |
| 10 | 2.5 | 0.00316 | 235.3 | 660 | 2.81 | 0.0089 | 12.1 | 2.6 | 89.8% | 98.6% |
| 11 | 2.5 | 0.00316 | 235.3 | 660 | 2.81 | 0.0089 | 14.1 | 3.5 | 86.4% | 98.2% |
| 12 | 2.2 | 0.00631 | 235.3 | 660 | 2.81 | 0.0177 | 11.1 | 3.5 | 91.5% | 98.5% |
| 13 | 2.2 | 0.00631 | 235.3 | 660 | 2.81 | 0.0177 | 14.7 | 3.5 | 89.9% | 98.5% |
| 14 | 2.2 | 0.00631 | 235.3 | 660 | 2.81 | 0.0177 | 8.8 | 3.5 | 91.1% | 99.1% |
| 15 | 2.2 | 0.00631 | 235.3 | 660 | 2.81 | 0.0177 | 9.3 | 3.5 | 91.2% | 99.0% |
| 16 | 2.2 | 0.00631 | 235.3 | 660 | 2.81 | 0.0177 | 6.2 | 3.5 | 92.0% | 99.2% |
| 17 | 2.2 | 0.00631 | 235.3 | 660 | 2.81 | 0.0177 | 11.9 | 3.5 | 94.0% | 98.8% |
| 18 | 1.7 | 0.01995 | 176.5 | 660 | 3.74 | 0.0746 | 8.0 | 3.5 | 91.3% | 99.5% |
| 19 | 2.0 | 0.01000 | 176.5 | 660 | 3.74 | 0.0374 | 7.9 | 3.5 | 91.9% | 99.4% |
| 20 | 1.8 | 0.01585 | 176.5 | 660 | 3.74 | 0.0593 | 7.9 | 3.5 | 92.3% | 99.1% |
| 21 | 1.8 | 0.01585 | 176.5 | 660 | 3.74 | 0.0593 | 9.0 | 0.5 | 93.1% | 99.0% |
| 22 | 1.8 | 0.01585 | 176.5 | 660 | 3.74 | 0.0593 | 8.9 | 0.5 | 92.8% | 99.1% |
| 23 | 1.8 | 0.01585 | 176.5 | 660 | 3.74 | 0.0593 | 9.0 | 0.25 | 92.8% | 99.1% |
| 24 | 1.8 | 0.01585 | 176.5 | 660 | 3.74 | 0.0593 | 9.5 | 0.125 | 92.6% | 98.9% |
| 25 | 1.8 | 0.01585 | 176.5 | 660 | 3.74 | 0.0593 | 10.9 | 0.06 | 90.7% | 99.2% |
| 26 | 1.2 | 0.06310 | 176.5 | 660 | 3.74 | 0.2360 | 18.0 | 0.5 | 91.2% | 99.1% |
| 27 | 1.8 | 0.01585 | 176.5 | 660 | 3.74 | 0.0593 | 17.1 | 0.5 | 93.5% | 99.1% |
| 28 | 3.5 | 0.00032 | 117.6 | 3000 | 25.50 | 0.0081 | 16.1 | 2.6 | 92.5% | 99.7% |
| 29 | 3.5 | 0.00032 | 117.6 | 3000 | 25.50 | 0.0081 | 23.2 | 2.6 | 93.0% | 99.7% |
| 30 | 3.5 | 0.00032 | 117.6 | 3000 | 25.50 | 0.0081 | 23.1 | 2.6 | 93.4% | 99.6% |

EXAMPLE 31

Pilot-plant Experiment

The apparatus used in this example consisted of a column having a diameter of 0.2 m, which was filled with 3.74 m high Sulzer BX packing and was fitted with a reflux divider. 0.4 m³/h of liquid were removed from the still of the column and passed through a phase separation vessel having a volume of 0.06 m³, where an organic phase separated out. The aqueous phase was reintroduced into the still of the column. The total volume of the still, the phase separation vessel and the connected pipework was 0.104 m³. The pH in the still of the column was monitored online and was 2.2. The proton concentration calculated therefrom was 0.00631 mol/l. The input of prenol was 10 l/h. Accordingly, the residence time concentration coefficient (RTCC) was 0.0656 h·mol/l. The reflux ratio was 16. During the experiment, 340 kg of prenol were added to the apparatus and the distillate formed was collected. 307 kg of DMVC in the form of a 74.9% strength by weight aqueous solution were obtained. The yield of DMVC was accordingly 90.3% of theory, and the purity was 98.5% (calculated on an anhydrous basis).

We claim:

1. A process for the continuous preparation of dimethylvinylcarbinol (DMVC) by continuously reacting prenol with the aqueous solution of a protic acid in the still or in the lower part of a rectification column while distilling off the DMVC formed in the form of an azeotropic mixture with water, which comprises
   a) during the reaction ensuring that as far as possible no liquid two-phase mixture forms in the reaction mixture,
   b) distilling off the DMVC which forms at a reflux ratio of at least 2 and
   c) setting the reaction volume and/or the amount of prenol added per hour and/or the concentration of protons in the reaction mixture in such a manner that the quotient, defined as residence time concentration coefficient, of the reaction volume and the volume of prenol added per hour multiplied by the concentration of protons in the reaction mixture has a value between 0.001 h·mol/l and 1 h·mol/l.

2. A process for the continuous preparation of dimethylvinylcarbinol as claimed in claim 1, which comprises, in order to prevent the formation of a liquid two-phase mixture in the reaction mixture, continuously taking from the latter a partial stream, passing it over a phase separation vessel, completely or at least largely removing there the small quantities, formed in the course of the reaction, of organic by-products which are insoluble or only partially soluble in water, and returning the aqueous phase to the reaction volume.

3. A process as claimed in claim 1, which comprises setting the reaction volume and/or the amount of prenol added per hour and/or the concentration of protons in the reaction mixture in such a manner that the quotient, defined as residence time concentration coefficient, of the reaction volume and the volume of prenol added per hour multiplied by the concentration of protons in the reaction mixture has a value between 0.01 h·mol/l and 0.15 h·mol/l.

4. A process as claimed in claim 1, which comprises distilling of the DMVC at a reflux ratio of from 2 to 25.

5. A process as claimed in claim 1, which comprises bringing the distillate obtained at the head of the column into close contact with an extractant which is only partially miscible with water, separating the organic phase which forms from the aqueous phase and returning the aqueous phase to the reaction volume.

6. A process as claimed in claim 5, which comprises separating the organic phase obtained at the head of the column in a rectification column, a mixture of a little DMVC, water and the extractant being obtained at the head thereof and pure DMVC being obtained from the still.

7. A process as claimed in claim 6, which comprises using the mixture of a little DMVC, a little water and the extractant, which is produced at the head of the rectification column, for extracting the distillate obtained at the head of the isomerization column.

8. A process as claimed in claim 1, which comprises carrying out the isomerization in a column having from 3 to 55 theoretical plates.

9. A process as claimed in claim 1, which comprises adjusting the pH of the aqueous solution of protic acid to from 1.2 to 3.5.

10. A process as claimed in claim 1, which comprises condensing the vapors leaving the head of the isomerization column and the vapors leaving the head of the rectification column in a common condenser.

11. A process as claimed in claim 4, wherein said reflux ratio is from 4 to 20.

* * * * *